US011324753B2

(12) United States Patent
Breder (10) Patent No.: US 11,324,753 B2
(45) Date of Patent: May 10, 2022

(54) METHOD OF TREATMENT OF ATTENTION DEFICIT/HYPERACTIVITY DISORDER (ADHD)

(71) Applicant: Supernus Pharmaceuticals, Inc., Rockville, MD (US)

(72) Inventor: Christopher D. Breder, Bethesda, MD (US)

(73) Assignee: Supernus Pharmaceuticals, Inc., Rockville, MD (US)

( * ) Notice: Subject to any disclaimer, the term of this patent is extended or adjusted under 35 U.S.C. 154(b) by 0 days.

(21) Appl. No.: 15/615,423

(22) Filed: Jun. 6, 2017

(65) Prior Publication Data
US 2017/0266195 A1 Sep. 21, 2017

Related U.S. Application Data (63) Continuation of application No. 14/634,281, filed on Feb. 27, 2015, which is a continuation of application No. 13/930,051, filed on Jun. 28, 2013, which is a continuation of application No. 12/585,157, filed on Sep. 4, 2009.

(60) Provisional application No. 61/094,502, filed on Sep. 5, 2008.

(51) Int. Cl.
*A61K 31/00* (2006.01)
*A61K 31/5375* (2006.01)

(52) U.S. Cl.
CPC .......... *A61K 31/5375* (2013.01); *A61K 31/00* (2013.01)

(58) Field of Classification Search
CPC .................................. A61K 31/5375
See application file for complete search history.

(56) References Cited

U.S. PATENT DOCUMENTS

| | | | |
|---|---|---|---|
| 3,714,161 | A | 1/1973 | Mallion et al. |
| 4,260,606 | A | 4/1981 | Cale, Jr. et al. |
| 5,558,879 | A | 9/1996 | Chen et al. |
| 5,658,590 | A | 8/1997 | Heiligenstein et al. |
| 6,046,193 | A | 4/2000 | Heiligenstein |
| 6,255,329 | B1 | 7/2001 | Maj |
| 6,586,427 | B2 | 7/2003 | Hassan et al. |
| 6,667,329 | B1 | 12/2003 | Maj |
| 6,964,962 | B2 | 11/2005 | Wong et al. |
| 9,358,204 | B2 | 6/2016 | Viera et al. |
| 9,662,338 | B2 | 5/2017 | Viera et al. |
| 10,265,319 | B2 | 4/2019 | Viera et al. |
| 2006/0003992 | A1 | 1/2006 | Wong et al. |
| 2006/0246134 | A1 | 11/2006 | Venkatesh |
| 2008/0014525 | A1 | 1/2008 | Sanders et al. |
| 2008/0153808 | A1 | 6/2008 | Gil et al. |
| 2010/0069390 | A1 | 3/2010 | Breder |
| 2010/0256106 | A1 | 10/2010 | Pasternak et al. |
| 2012/0115871 | A1 | 5/2012 | Breder |

FOREIGN PATENT DOCUMENTS

| | | |
|---|---|---|
| GB | 2047096 A | 11/1980 |
| JP | 2005-504052 A | 2/2005 |
| JP | 2008-507483 A | 3/2008 |
| JP | 2009-526021 A | 7/2009 |
| WO | WO 99/15177 A1 | 4/1999 |
| WO | WO 2006/010457 A2 | 2/2006 |
| WO | WO 2007/026219 A2 | 3/2007 |
| WO | WO 2008/061226 A2 | 5/2008 |
| WO | WO 2008/122019 A1 | 10/2008 |
| WO | WO-2008/157094 A1 | 12/2008 |
| WO | WO 2008/157094 A1 | 12/2008 |
| WO | WO-2010/127120 A1 | 11/2010 |
| WO | WO 2011/008298 A2 | 1/2011 |

OTHER PUBLICATIONS

Altamura et al., "Age, Therapeutic 'Milieu' and Clinical Outcome in Depressive Patients Treated with Viloxazine: A Study with Plasma Levels," Progress in Neuro-Psychopharmacology & Biological Psychiatry, Oxford, GB, 1986, 10:67-75.

Bayliss et al., "Blood Level Studies with Voxazine Hydrochloride in Man," Br. J. Clin. Pharmac., Jun. 1975, 2(3):209-214.

Chebili et al., "Antidepressants and sexual stimulation: the correlation," Encephale, May-Jun. 1998, 24(3):180-184, English abstract only.

Giles et al., "Characterization of a 5-HT$_{1B}$ receptor on CHO cells: functional responses in the absence of radioligand binding," British Journal of Pharmacology, 1996, 117:1119-1126.

Goodman & Gilman's: The Pharmacological Basis of Therapeutics, 10$^{th}$ Edition, 2001, 474-477.

Hedlund et al., "5-HT$_7$ receptor inhibition and inactivation induce antidepressant like behavior and sleep pattern," Biol. Psychiatry, 2005, 58(10):831-837.

Lucchelli et al., "The interaction of antidepressant drugs with enteric 5-HT$_7$ receptors," Naunyn-Schmiedebergs Arch. Pharmacol., 2000;362(3):284-289.

Rojo, R. Gomez, "Double blind controlled study of viloxazine and imipramine in depression," Hospital General, 1976, 16(1):27-38, with English summary on p. 37.

Streubel et al., "Gastroretentive drug delivery systems," Expert Opinion Drug Delivery, 2006, 3(2):217-233.

Tatsumi et al., "Pharmacological profile of antidepressants and related compounds at human monoamine transporters," Eur. J. Pharmacol., 1997, 340(2-3):249-258.

Vanhoenacker et al., "5-HT$_7$ receptors: current knowledge and future prospects," Trends Pharmacol. Sci., 2000, 21(2):70-77.

Findling et al., "Viloxazine in the Management of CNS Disorders: A Historical Overview and Current Status," CNS Drugs, 2021, 35:643-653.

Garcia-Olivares et al., "Effects of Viloxazine on Central Neurotransmitter Systems: A Microdialysis Study in Freely Moving Rats," ASENT 2020, Mar. 2-5, 2020, abstract, 1 page.

(Continued)

Primary Examiner — Yong S. Chong
(74) Attorney, Agent, or Firm — Foley & Lardner LLP (57) ABSTRACT The invention comprises a method for treatment of ADHD or ADHD-related disorders by a pharmaceutical agent exhibiting combined serotonergic or noradrenergic reuptake transporters and monoamine receptor activity.

9 Claims, 6 Drawing Sheets

(56) References Cited

OTHER PUBLICATIONS

Garcia-Olivares et al., "Effects of Viloxazine on Central Neurotransmitter Systems: A Microdialysis Study in Freely Moving Rats," ASENT 2020, Mar. 2-5, 2020, poster, 1 page.

Maletic, Vladimir, "An Evaluation of SPN-812 (Viloxazone Extended-Release) in the Treatment of Pediatric Patients with ADHD: From Mechanism to Efficacy," APSARD, Jan. 17-19, 2020, presentation, 47 pages.

Maletic, Vladimir, "Multimodal mechanism of action of viloxazine: serotonin and norepinephrine modulating properties," GME, 2020, presentation, 4 pages.

Yu et al., "Mechanism of action of viloxazine: effects on norepinephrine and serotonin," APSARD, Jan. 15-17, 2021, abstract, 1 page.

Yu et al., "Mechanism of action of viloxazine: effects on norepinephrine and serotonin," APSARD, Jan. 15-17, 2021, poster, 1 page.

Yu et al., "Mechanism of action of viloxazine: effects on serotonin and norepinephrine," GME, 2020, abstract, 1 page.

Yu et al., "Mechanism of action of viloxazine: effects on serotonin and norepinephrine," GME, 2020, poster 1 page.

Yu et al., "Mechanism of action of viloxazine: effects on serotonin and norepinephrine," NEI, November May 8, 2020, poster, 1 page.

Yu et al., "Multimodal mechanism of action of viloxazine: serotonin and norepinephrine modulating properties," ACNP, Dec. 6-9, 2020, abstract, 1 page.

Yu et al., "Multimodal mechanism of action of viloxazine: serotonin and norepinephrine modulating properties," APSARD, Jan. 17-19, 2020, abstract, 1 page.

Yu et al., "New Insights into the Mechanism of Action of Viloxazine: Serotonin and Norepinephrine Modulating Properties," Journal of Experimental Pharmacology, 2020, 12:285-300.

METHOD OF TREATMENT OF ATTENTION DEFICIT/HYPERACTIVITY DISORDER (ADHD)

CROSS-REFERENCE TO RELATED APPLICATIONS

This application is a Continuation of U.S. application Ser. No. 14/634,281, filed Feb. 27, 2015, which is a Continuation of U.S. application Ser. No. 13/930,051, filed Jun. 28, 2013, which is a Continuation of U.S. application Ser. No. 12/585,157, filed Sep. 4, 2009, which claims priority from U.S. Provisional Application No. 61/094,502, filed Sep. 5, 2008. The entire contents of the aforementioned applications are incorporated herein by reference.

BACKGROUND

Viloxazine (Emovit®, Vivalan®, Vivarin®, Vicilan®) is a bicyclic antidepressant morpholine derivative that inhibits the reuptake of norepinephrine. Viloxazine hydrochloride has been approved in Italy, Belgium, England, Ireland, Germany, Portugal, Spain, the former Yugoslavia, France, Slovakia, for the treatment of major depressive disorder.

Viloxazine is known to inhibit noradrenergic reuptake transporters (155 nM) and has very weak activity at the serotonin reuptake inhibitor (17.3 µm). (Tatsumi et al [1997] Eur J Pharmacol 340 (2-3): 249-58).

The present invention is predicated on the unexpected discovery that viloxazine may be effective in the treatment of ADHD in humans with nominal, if any, significant side effects.

SUMMARY OF THE INVENTION

In one embodiment of the invention, a method of treating ADHD and ADHD-related disorders in a mammal comprising administering to the mammal a pharmaceutical agent exhibiting 5HT1B and/or 5HT7 antagonistic activity is provided.

In another embodiment, the invention provides a method for treatment of ADHD and ADHD-related disorders in a mammal comprising administering to the mammal a pharmaceutical agent exhibiting a combination of at least two of the following: noradrenergic reuptake inhibitory activity, 5HT1B antagonistic activity, and 5HT7 antagonistic activity.

In yet another embodiment, the invention provides a method for treatment of ADHD and ADHD-related disorders in a mammal comprising administering to the mammal a pharmaceutical agent exhibiting a combination of at least two of the following: noradrenergic reuptake inhibitory activity, $\alpha 4/\beta 2$ antagonistic activity, and $\alpha 7$ antagonistic activity.

In still another embodiment, the invention provides a method for treatment of ADHD and ADHD-related disorders in a mammal comprising administering to the mammal a pharmaceutical agent exhibiting a combination of at least two of the following: 5HT1B antagonistic activity, 5HT7 antagonistic activity, $\alpha 4/\beta 2$ antagonist activity, and $\alpha 7$ antagonistic activity.

In another embodiment, the current invention provides a novel method for treatment of ADHD and related disorders by administering a formulation of viloxazine.

The invention also provides a method of identifying compounds for the treatment of ADHD and/or similar disorders.

DETAILED DESCRIPTION OF THE INVENTION

Unless otherwise specified, "a" or "an" means "one or more."

In one embodiment, the invention provides a method for treatment of ADHD and ADHD-related disorders. ADHD-related disorders include, but are not limited to, mood or affective disorders such as anxiety, depression or bipolar disorder; or disorders where ADHD may be a co-morbid syndrome, such as obsessive compulsive disorder, Tourette's Syndrome, or Post Traumatic Stress Disorder. The method comprises the administration to a mammal diagnosed with ADHD or an ADHD-related disorder a pharmaceutical agent exhibiting a combination (at least 2) of: noradrenergic reuptake inhibitory activity, 5HT1B antagonistic activity, and 5HT7 antagonistic activity. In another embodiment, the invention comprises a method of treating any of the above-listed disorders with a pharmaceutical agent exhibiting a combination (at least 2) of: noradrenergic reuptake inhibitory activity, $\alpha 4/\beta 2$ antagonistic activity, and $\alpha 7$ antagonistic activity. In still another embodiment, the invention comprises a method of treating any of the above-listed disorders with a pharmaceutical agent exhibiting a combination (at least 2) of: 5HT1B antagonistic activity, 5HT7 antagonistic activity, $\alpha 4/\beta 2$ antagonistic activity, and $\alpha 7$ antagonistic activity.

The pharmaceutical agents suitable for invention are identified by a process comprising the steps of: (1) selecting one or a combination of active agents with known activity inhibiting either serotonin or noradrenergic reuptake transporters; (2) conducting a receptor screening assay on the selected agent(s) to identify activity on at least one nicotinic, dopaminergic, serotonergic or gabaergic receptor or binding site where the activity is known to be associated with ADHD; (3) determining if said activity is agonistic or antagonistic; (4) selecting among the screened active agents at least one that targets the most of the different types of ADHD-associated receptors; and (5) optimizing the total dosage of the selected active agent(s).

In a preferred embodiment of the invention, the pharmaceutical agent is viloxazine. The present inventor unexpectedly discovered that in addition to noradrenergic activity, viloxazine exhibits specific antagonist activity at the 6-HT7 (serotonin 7) and 5HT1B receptors. It was also discovered that viloxazine exhibits $\alpha 4/\beta 2$ and/or $\alpha 7$ antagonistic activity. This heretofore unknown receptor activity of viloxazine was evaluated as follows:

I. Viloxazine Activity on 5-HT Receptors

A heterologous competition assay was used to determine the relative affinity of viloxazine for 5-HT receptors. Briefly, recombinant 5-HT1B OR 5-HT7 receptors were expressed in a CHO cell line. The receptors were then saturated with a tritiated receptor-specific ligand at concentrations known to be saturating. Thereupon, 10 μM viloxazine was added to the cells in the presence of non-specific ligand and incubated. In this way, viloxazine was allowed to "compete" with the receptor-specific ligand, such that greater displacement (i.e., % inhibition) is indicative of greater binding strength of viloxazine at a given receptor. "Specific binding" refers here to the difference in the binding of the ligand to the receptors in the presence or absence of an excess of the viloxazine. The conditions and results of the assays are summarized in the Table 1.

TABLE 1

Conditions of the displacement assay at select serotonin receptors for viloxazine

| Receptor | Ligand | Conc. | Non-specific | Incubation | % Inhib. | Detection method |
|---|---|---|---|---|---|---|
| 5-HT1A (h) | [3H]8-OH-DPAT | 0.3 nM | 8-OH-DPAT (10 μM) | 60 min/22° C. | 66 | Scintillation counting |
| 5-HT1B | [125I]CYP (+30 μM (—)propranolol) | 0.1 nM | serotonin (10 μM) | 120 min/37° C. | 78 | Scintillation counting |
| 5-HT1D | [3H]serotonin | 1 nM | serotonin (10 μM) | 60 min/22° C. | 18 | Scintillation counting |
| 5-HT2A (h) | [3H]ketanserin | 0.5 nM | ketanserin (1 μM) | 60 min/22° C. | −17* | Scintillation counting |
| 5-HT2C (h) | [3H]mesulergine | 1 nM | RS-102221 (10 μM) | 60 min/37° C. | 56 | Scintillation counting |
| 5-HT3 (h) | [3H]BRL 43694 | 0.5 nM | MDL 72222 (10 μM) | 120 min/22° C. | 18 | Scintillation counting |
| 5-HT4e (h) | [3H]GR 113808 | 0.3 nM | serotonin (100 μM) | 60 min/37° C. | 16 | Scintillation counting |
| 5-HT5A (h) | [3H]LSD | 1 nM | serotonin (100 μM) | 60 min/37° C. | 15 | Scintillation counting |
| 5-HT6 (h) | [3H]LSD | 2 nM | serotonin (100 μM) | 120 min/37° C. | 6 | Scintillation counting |
| 5-HT7 (h) | [3H]LSD | 4 nM | serotonin (10 μM) | 120 min/22° C. | 70 | Scintillation counting |

*A negative number reflects negligible inhibition, i.e., a condition where the binding of the radioactive test ligand was greater in the presence of viloxazine. This reflects either the variability in the radioactive control ligand binding or facilitation by the test ligand.

Figure 1:
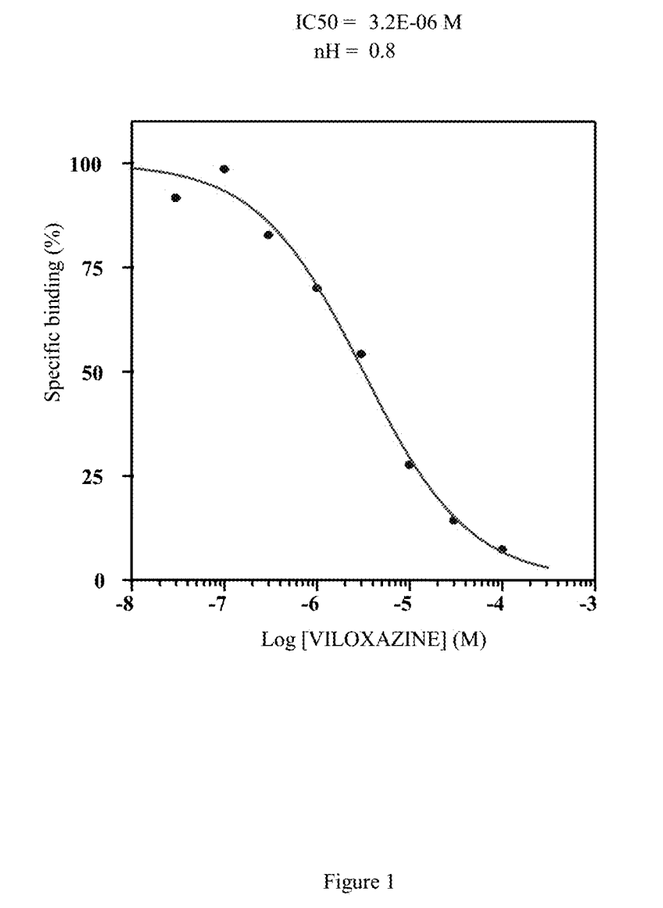
FIG. 1 shows a competition curve obtained with compound viloxazine with human 5-HT7 receptor.

The affinity of viloxazine for 5-HT7 5-HT1B receptors was further characterized by determining the IC50 (i.e., the concentration of viloxazine that can inhibit 50% of control specific binding). For this experiment, a range of viloxazine concentrations was selected for the ligand blocking assay. The IC50 was determined using non-linear regression analysis of the competition curves using a Hill equation curve fitting $(Y=D+[(A-D)/(1+(C/C50)nH)])$, where $Y$=specific binding, $D$=minimum specific binding, $A$=maximum specific binding, $C$=compound concentration, $C50$=IC50, and $nH$=slope factor). The inhibition constants Ki were calculated using Cheng Prusoff equation. Ki is defined as the concentration of the competing ligand (viloxazine) that bound to half the binding sites at equilibrium in the absence of radioligand or other competitors. The results of the affinity assay are summarized in Tables 2 and 3, and in FIG. 1.

TABLE 2

| | | % of Control Specific Binding | | |
|---|---|---|---|---|
| Receptor | Concentration (M) | 1st | 2nd | Mean |
| 5-HT1A (h) | 3.0E−08 | 97.8 | 99.8 | 98.8 |
| | 1.0E−07 | 93.8 | 96.9 | 95.4 |
| | 3.0E−07 | 104.7 | 110.3 | 107.5 |
| | 1.0E−06 | 104.8 | 109.1 | 107.0 |
| | 3.0E−06 | 76.5 | 71.4 | 73.9 |
| | 1.0E−05 | 32.5 | 41.3 | 36.9 |
| | 3.0E−05 | 21.9 | 19.6 | 20.7 |
| | 1.0E−04 | 5.3 | 5.8 | 5.5 |
| 5-HT1B | 3.0E−08 | 102.0 | 99.9 | 101.0 |
| | 1.0E−07 | 97.6 | 92.4 | 95.0 |
| | 3.0E−07 | 92.4 | 82.7 | 87.6 |
| | 1.0E−06 | 77.7 | 79.0 | 78.4 |
| | 3.0E−06 | 61.5 | 52.6 | 57.1 |
| | 1.0E−05 | 36.6 | 27.1 | 31.9 |

TABLE 2-continued

| | | % of Control Specific Binding | | |
|---|---|---|---|---|
| Receptor | Concentration (M) | 1st | 2nd | Mean |
| | 3.0E−05 | 13.7 | 4.5 | 9.1 |
| | 1.0E−04 | −10.4 | −12.4 | −11.4 |
| 5-HT2C (h) | 3.0E−08 | 97.9 | 125.8 | 111.9 |
| | 1.0E−07 | 116.6 | 111.5 | 114.0 |
| | 3.0E−07 | 92.9 | 102.7 | 97.8 |
| | 1.0E−06 | 108.2 | 104.2 | 106.2 |

TABLE 2-continued

| | | % of Control Specific Binding | | |
|---|---|---|---|---|
| Receptor | Concentration (M) | 1st | 2nd | Mean |
| | 3.0E−06 | 90.6 | 91.9 | 91.3 |
| | 1.0E−05 | 61.6 | 63.1 | 62.3 |
| | 3.0E−05 | 33.1 | 36.6 | 34.8 |
| | 1.0E−04 | 8.4 | 14.3 | 11.4 |
| 5-HT7 (h) | 3.0E−08 | 90.6 | 92.7 | 91.7 |
| | 1.0E−07 | 102.9 | 94.2 | 98.5 |
| | 3.0E−07 | 80.4 | 85.1 | 82.7 |
| | 1.0E−06 | 73.5 | 66.5 | 70.0 |
| | 3.0E−06 | 48.2 | 60.2 | 54.2 |
| | 1.0E−05 | 27.3 | 27.9 | 27.6 |
| | 3.0E−05 | 15.3 | 13.2 | 14.3 |
| | 1.0E−04 | 6.5 | 8.1 | 7.3 |

TABLE 3

Summary of IC50 determination at select serotonin receptors for Viloxazine.

| Assay | Reference compound | IC50 (M) | Ki (M) | n (H) |
|---|---|---|---|---|
| 5-HT1A (h) | 8-OH-DPAT | 7.1E−06 | 4.5E−06 | 1.3 |
| 5-HT1B | serotonin | 3.8E−06 | 2.3E−06 | 1.0 |
| 5-HT2C (h) | RS-102221 | 1.4E−05 | 6.4E−06 | 1.0 |
| 5-HT7 (h) | serotonin | 3.2E−06 | 1.2E−06 | 0.8 |

The nature of the binding (i.e., agonist or antagonist) was next determined. Briefly, an assay was designed that examined the agonist effect on the 5HT7 or 5-HT1B receptor, i.e., the generation of cAMP or the blockade of this effect when stimulated by a 5HT7 agonist, serotonin. This was also done with a range of concentrations to determine the relative agonist versus antagonist binding Ki. The EC50 values (concentration producing a half-maximal specific response)

and IC50 values (a concentration causing a half-maximal inhibition of the control-specific agonist response) were determined by a non-linear regression analysis of the concentration-response curves generated with mean replicate values using Hill equation curve fitting. The apparent dissociation constants for antagonists Kb were calculated using the modified Cheng Prusoff equation.

Figure 2:
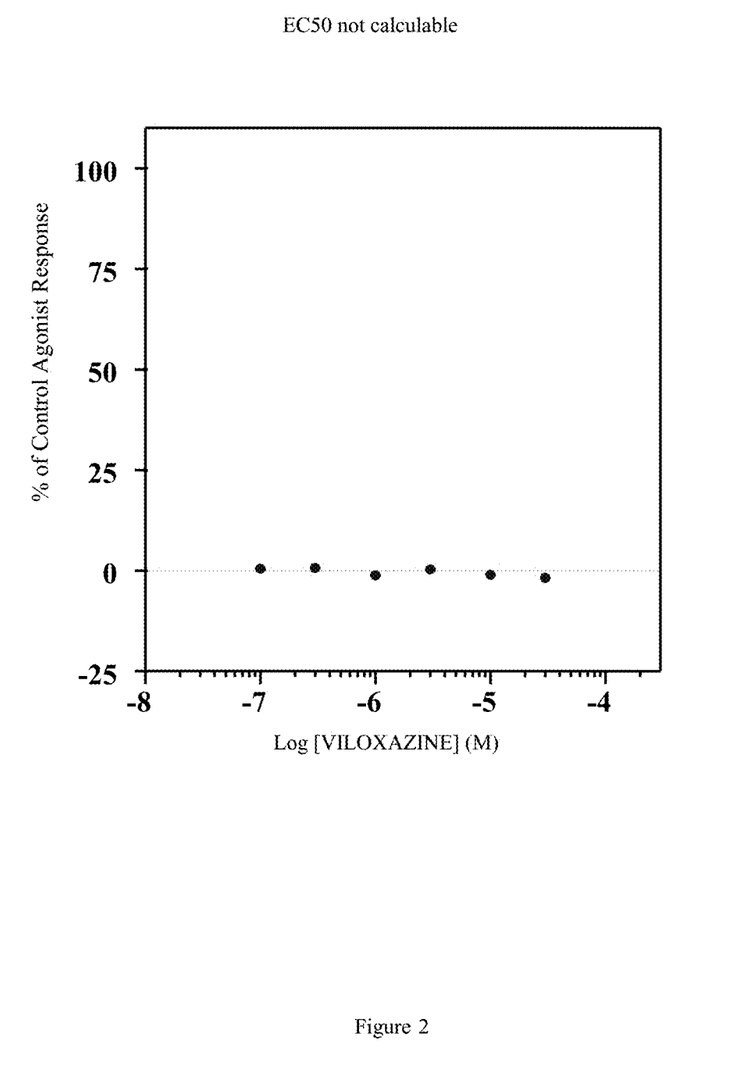
FIG. 2 shows the agonist effect of the compound viloxazine with human 5HT7 receptor.
Figure 3:
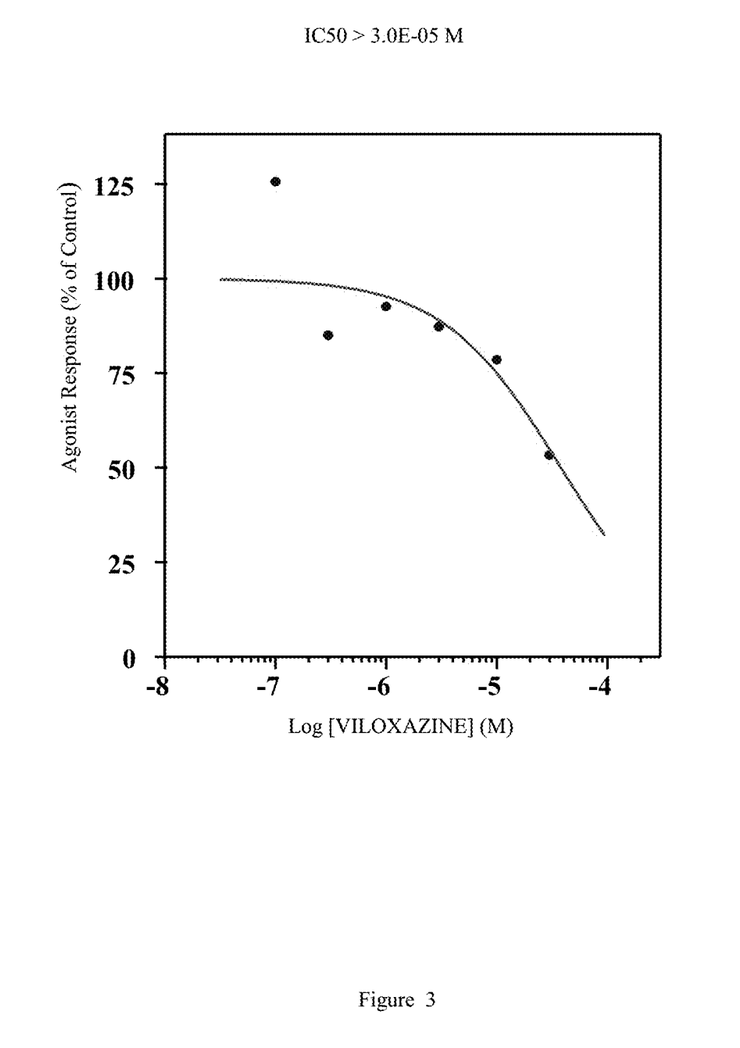
FIG. 3 shows the antagonist effect of the compound viloxazine with human 5HT7 receptor.
Figure 4:
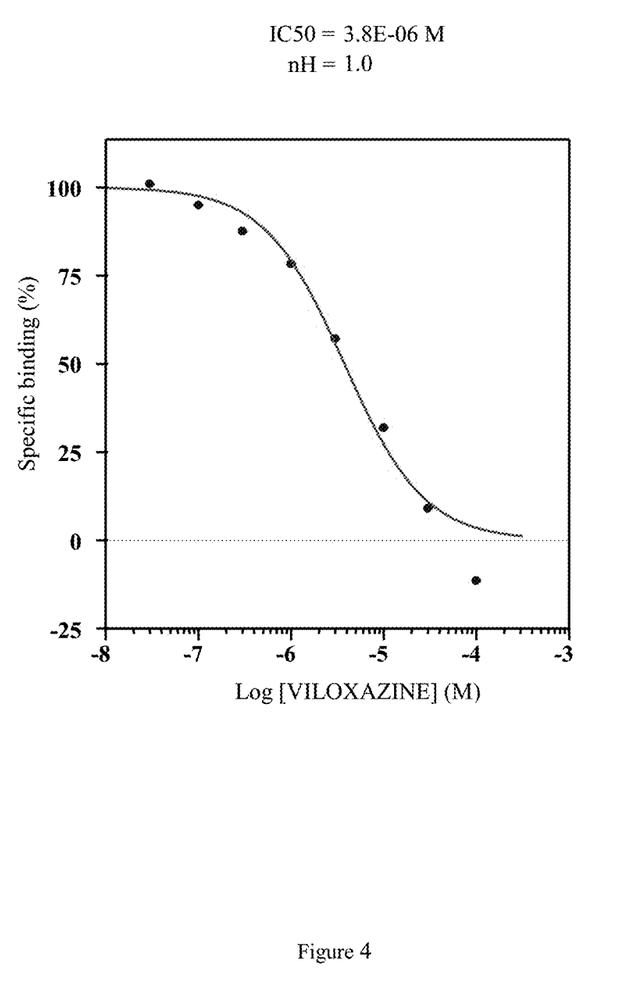
FIG. 4 shows a competition curve obtained with compound viloxazine with human 5-HT1B receptor.
Figure 5:
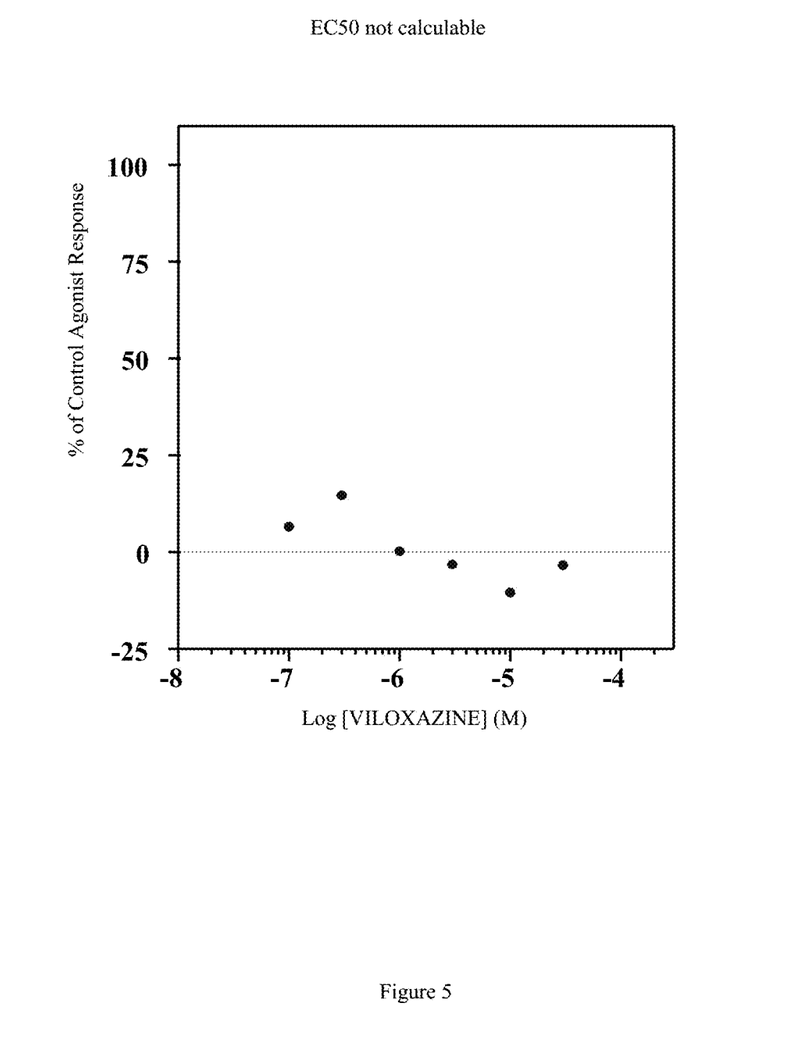
FIG. 5 shows the agonist effect of the compound viloxazine with human 5HT1B receptor.
Figure 6:
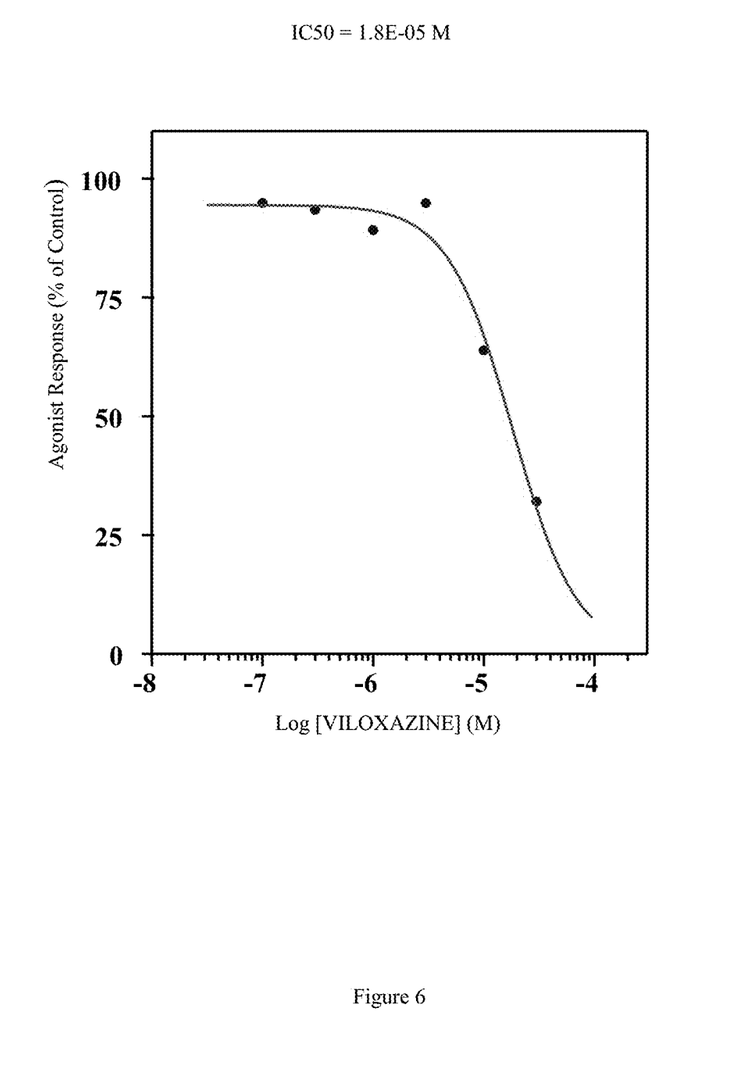
FIG. 6 shows the antagonist effect of the compound viloxazine with human 5HT1B receptor.

The conditions of the screening are represented in Table 4. Results of the functional assays are seen in FIGS. 2 (5-HT7 agonist assay) and 3 (5-HT7 antagonist assay). The agonist assay demonstrated no measurable response (FIG. 2). The antagonist assay for 5-HT7 yielded a weak response with an IC50 greater than $3.0 \times 10^{-5}$ M.

TABLE 4

Conditions for 5HT7 Functional Assay

| Assay | Reference compound | Incubation conditions | Reaction product | Method of detection |
|---|---|---|---|---|
| 5-HT7 (h) (agonist effect) | none | 45 min/37° C. | cAMP | HTRF |
| 5-HT7 (h) (antagonist effect) | serotonin | 45 min/37° C. | cAMP | HTRF |
| 5-HT1B (h) (agonist effect) | none | 30 min/37° C. | cAMP | HTRF |
| 5-HT1B (h) (antagonist effect) | serotonin | 30 min/37° C. | cAMP | HTRF |

II. Viloxazine Activity on Nicotinic Receptors

Conditions for the Initial Screen:

Membrane homogenates of rat cerebral tissue are incubated with 1.5 nM [3H]cystine (for nicotinic acetylcholine α4β2 screen) or 1 nM [125]α-bungarotoxin (for nicotinic acetylcholine α7 screen) in the absence or presence of 10 μM test compound in buffer. Nonspecific binding is determined in the presence of 10 μM nicotine for α4β2 or 1 μM α-bungarotoxin for α7. Following incubation, the samples are filtered rapidly under vacuum through glass fiber filters and rinsed several times. The filters are dried, then counted for radioactivity in a scintillation counter. The results can be expressed as a percent inhibition of the control radioligand specific binding. The standard reference compound is nicotine for α4β2 and α-bungarotoxin for α7, which is tested in each experiment at several concentrations to obtain a competition curve from which its IC50 can be calculated. Conditions for the IC50 determination can be the same as for the initial screen, except the test compound is assayed at 8 different concentrations between 10-9 and 10-4 M.

The effectiveness of viloxazine for ADHD treatment can be evaluated in a Five-Choice Serial Reaction Time Task (5-CSRTT) assay. This test in typically performed with rats and is designed to show brain regions and neural substrates involved in attention, information processing speed, impulsivity, hyperactivity and preservative behaviors (obsessive compulsive disorder-like). Pharmaceutical agents of the current invention, including but not limited to viloxazine, can be tested to measure their effects on attention, impulsivity and reaction time and the outcome analyzed to determine their profile and application to treating ADHD.

An additional test, SmartCube™, can also be performed to obtain a "behavioral signature" for a given compound. The experimental platform of this test combines robotics, computer video capture and analysis (called computer vision), and bioinformatics to capture and analyze data.

An animal treated with the test compound under study is placed in an enclosure and presented with a non-invasive behavioral challenge, such as changing the floor's configuration. The animal's behavior is recorded using cameras and electro-mechanical sensors, and data from these recordings are processed using algorithms to reveal the compound's behavioral signature. This "signature" can then be screened against the company's database of signatures from reference compounds to identify candidates predicted to have utility in treating ADHD.

According to the invention, ADHD or ADHD-related disorders can be treated in human subjects by administering viloxazine in a total daily dose that is at least 10% lower than the current minimally effective dose of 2.14 mg/kg, which is used to treat major depressive disorder. In other embodiments, the dose is 15% lower, 25% lower, 35% lower, or 50% lower than the current dose. Dosage ranges of 1.1 mg/kg/day to 9.7 mg/kg/day or approximately 20 to 800 mg for pediatric (aged 6 to 17) and adult population are also provided.

According to the invention, viloxazine can be administered in the amount of from 10 to 600 mg/day. In another embodiment, the daily dose of viloxazine may be from 150 to 400 mg/day. In yet further embodiment of the invention, viloxazine is administered in the amount of up to 300 mg/day. The method of the current invention offers a safe and effective treatment of ADHD and related disorders in both children and adults. For the purposes of this invention, a term "viloxazine" includes viloxazine and all pharmaceutically acceptable salts thereof, as well as all isomers, stereomers and polymorphs thereof.

In another embodiment, the invention encompasses a method of treatment of ADHD or ADHD-related disorders with viloxazine that is characterized by an improved adverse effect profile. The adverse effects that are diminished by the method of the present invention include, but are not limited to, nausea, vomiting, insomnia, loss of appetite, increased erythrocyte sedimentation, EKG and EEG anomalies, epigastric pain, diarrhea, constipation, vertigo, orthostatic hypotension, edema of the lower extremities, dysarthria, tremor, psychomotor agitation, mental confusion, inappropriate secretion of antidiuretic hormone, increased transaminases, seizure, and increased libido. Hence, the inventive method provides for the treatment of ADHD without, or at least with far less frequency than with conventional viloxazine-treatment, of one, two, six or more of these listed side effects. The efficacy and the adverse effect profile of the lower dose treatment of the current invention can be evaluated in a randomized, placebo controlled trial.

Whereas particular embodiments of the invention have been described herein for the purpose of illustrating the invention and not for the purpose of limiting the same, it will be appreciated by those of ordinary skill in the art that numerous variations of the details, materials and arrangement of parts may be made within the principle and scope of the invention without departing from the invention as described in the appended claims.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention.

All of the publications, patent applications and patents cited in this specification are incorporated herein by reference in their entirety.

REFERENCES

1. Vanhoenacker P, Haegeman G, Leysen J E. 5-HT7 receptors: current knowledge and future prospects. Trends Pharmacol Sci 2000; 21(2):70-7.

2. Lucchelli A, Santagostino-Barbone M G, D'Agostino G, Masoero E, Tonini M. The interaction of antidepressant drugs with enteric 5-HT7 receptors. Naunyn Schmiedebergs Arch Pharmacol 2000; 362(3):284-9.
3. Hedlund P B, Huitron-Resendiz S, Henriksen S J, Sutcliffe J G. 5-HT7 receptor inhibition and inactivation induce antidepressant like behavior and sleep pattern. Biol Psychiatry 2005; 58 (10):831-7.
4. Giles H, Lansdell H J, Bolofo M L, Wilson H L, and Martin G R. Characterization of a $5-HT_{1B}$ receptor on CHO cells: functional responses in the absence of radioligand binding. Br J Pharmacol 1996: 117:1119-26.

What is claimed is:

1. A method of antagonizing 5-HT7 and 5HT1B receptor activity in a patient suffering from ADHD, consisting of administering to the patient in need thereof a therapeutically effective amount of viloxazine, wherein the administration antagonizes both receptors.

2. The method of claim 1, wherein the therapeutically effective amount is from about 20 to about 800 mg a day.

3. The method of claim 1, wherein the therapeutically effective amount is from about 10 to about 600 mg a day.

4. The method of claim 3, wherein the therapeutically effective amount is from about 150 to about 400 mg a day.

5. The method of claim 4, wherein the therapeutically effective amount is from 150 to 300 mg a day.

6. The method of claim 1, which provides an improved adverse effect profile.

7. The method of claim 1, wherein the patient is a human child.

8. The method of claim 1, wherein the patient further suffers from anxiety, depression, or bipolar disorder.

9. The method of claim 1, wherein the patient further suffers from obsessive compulsive disorder, Tourette's Syndrome, or Post Traumatic Stress Disorder.

* * * * *